(12) United States Patent
Vega et al.

(10) Patent No.: US 7,272,860 B2
(45) Date of Patent: Sep. 25, 2007

(54) PROTECTIVE FACE SHIELD ADJUSTMENT SYSTEM

(76) Inventors: Anthony Vega, 2514 Savannah Ave., El Paso, TX (US) 79930; Alvaro Aburto-Garcia, 3584 Greenveil Dr., El Paso, TX (US) 79936

( * ) Notice: Subject to any disclaimer, the term of this patent is extended or adjusted under 35 U.S.C. 154(b) by 204 days.

(21) Appl. No.: 10/965,741

(22) Filed: Oct. 18, 2004

(65) Prior Publication Data

US 2006/0081262 A1 Apr. 20, 2006

(51) Int. Cl.
*A41D 13/00* (2006.01)

(52) U.S. Cl. .............................................. 2/9; 128/846
(58) Field of Classification Search ................ 2/9, 2/12, 15; 351/41; 128/846
See application file for complete search history.

(56) References Cited

U.S. PATENT DOCUMENTS

| | | | |
|---|---|---|---|
| 2,881,443 A * | 4/1959 | Barker, Jr. ........................ 2/9 |
| 4,812,142 A | 3/1989 | Brodmann |
| 4,856,535 A * | 8/1989 | Forbes ....................... 128/857 |
| 4,872,465 A * | 10/1989 | Kuntz et al. ................ 128/857 |
| 4,937,880 A | 7/1990 | Beard |
| 4,965,887 A | 10/1990 | Paoluccio |
| 4,986,282 A | 1/1991 | Stackhouse et al. |
| 4,989,463 A | 2/1991 | Cimaglia |
| 5,113,528 A | 5/1992 | Burke, Jr. et al. |
| 5,224,940 A | 7/1993 | Dann |
| 5,299,582 A | 4/1994 | Potts |
| 5,440,760 A | 8/1995 | Highsmith |
| 5,446,925 A | 9/1995 | Baker et al. |
| 5,584,078 A | 12/1996 | Saboory |
| 5,592,698 A | 1/1997 | Woods |
| 5,634,210 A * | 6/1997 | King et al. ........................ 2/9 |
| 5,647,060 A | 7/1997 | Lee |
| 5,692,235 A | 12/1997 | Fields |
| 5,765,223 A | 6/1998 | McCausland |
| 5,797,141 A | 8/1998 | Morlett |
| 5,899,206 A * | 5/1999 | La Chappelle-Reynolds .... 128/846 |
| 6,038,705 A | 3/2000 | Jarvis |
| 6,079,980 A * | 6/2000 | Durand ....................... 433/137 |
| 6,564,804 B2 | 5/2003 | Salatka |
| 6,790,192 B2 * | 9/2004 | Robinson ..................... 602/21 |

* cited by examiner

*Primary Examiner*—Katherine Moran
(74) *Attorney, Agent, or Firm*—Banner & Witcoff, Ltd.

(57) ABSTRACT

A system and apparatus for protecting the face of a user while allowing for adjustment of the size of the protected area are described. A protective face shield includes a substantially flat, at least partially transparent, waterproof sheet material of a shape configured to extend over the face of a user, where the sheet material includes a portion configured to assist in the modification of the size of the sheet material. The portion may include predefined lines and notches corresponding to different sizes that the sheet material may be trimmed to achieve. An adhesive component secures the sheet material to the face of the user. The sheet material also may include indicium corresponding to a size of the face shield, user specific information, and/or other information.

12 Claims, 9 Drawing Sheets

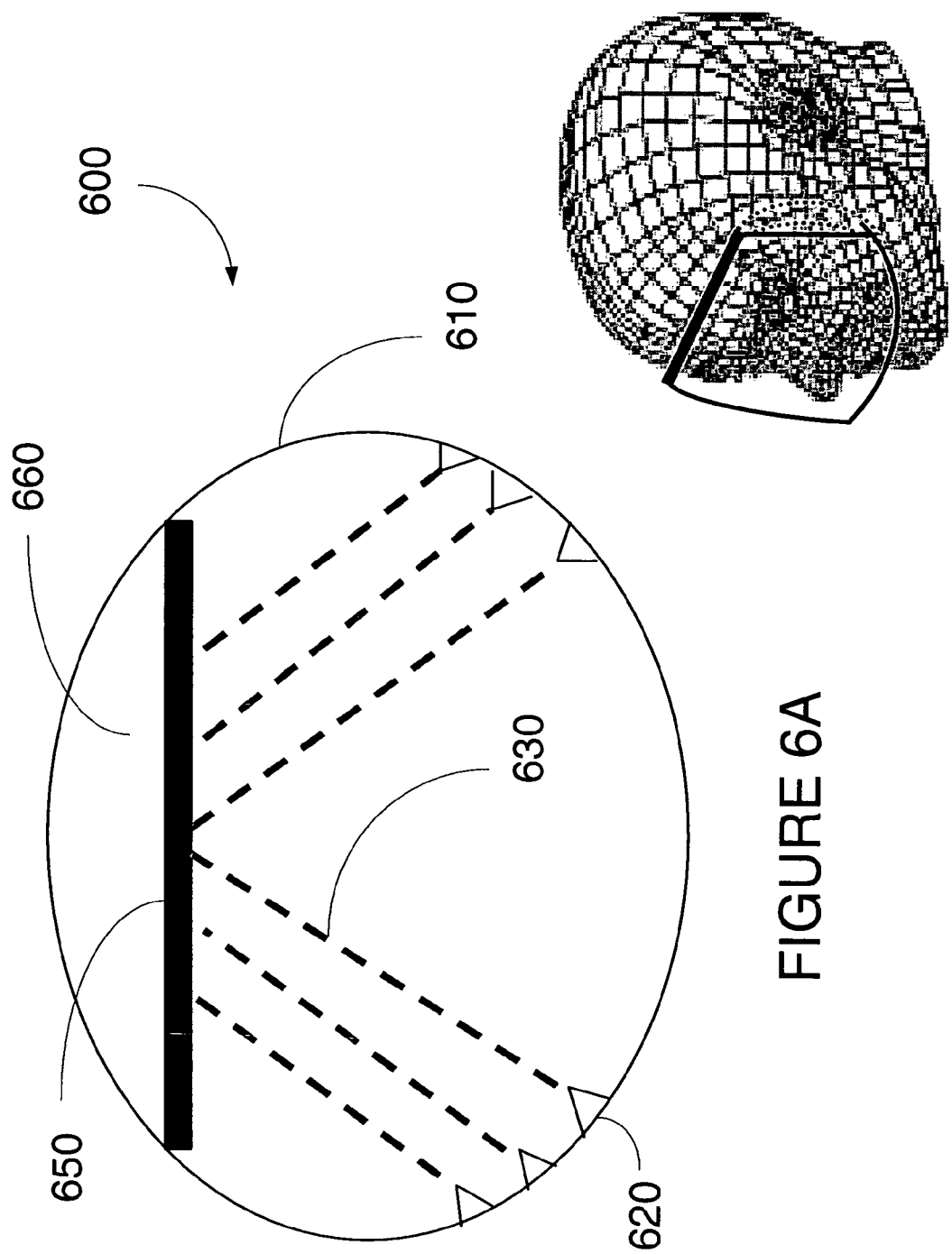

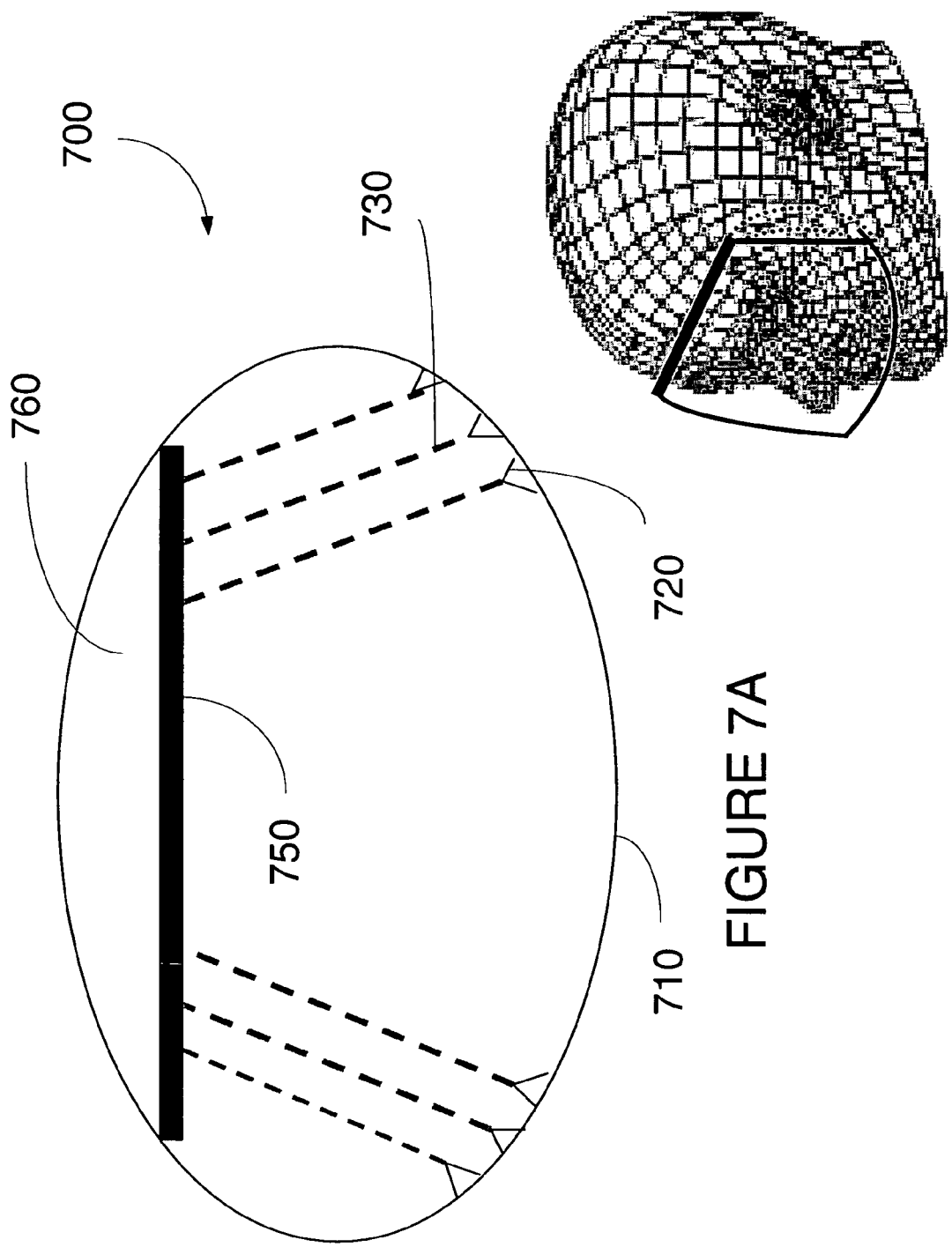

PROTECTIVE FACE SHIELD ADJUSTMENT SYSTEM

FIELD OF THE INVENTION

The invention relates generally to a system and apparatus for protecting the face of a user. More specifically, the invention provides a disposable protective face shield that includes an adjustment system allowing a user to orient the face shield to a desired configuration on the user's face.

BACKGROUND OF THE INVENTION

With the increase of both elective and necessary facial and eye surgeries over the years, a demand for increased ease of protecting the face of a patient after surgery has increased. A patient may have bandages or stitches over areas of her face needing protection from dust and/or water. A user may wish to get back to a daily routine after a facial surgery but is prevented from certain activities for the consequences associated with exposure to water and/or dust. For example, a patient may want to take a shower but is forced to take a bath in order to ensure that no water splashes on her face.

Conventional protective face shield use an adhesive or belt strap system to stick the face shield against the face of a user. The user is thus protected against water and dust when wearing the face shield. However, conventional face shields have a predefined shape that fails to allow for easy or cost-effective adjustment. FIG. 1 is an example of a conventional face shield 100 including a few methods of adjustment of the fit of the face shield. Face shield 100 includes two different systems for adjusting the fit. A belt system 103 allows a user to tighten a strap wrapping around the top of the head of the user. In addition, a screw system 105 tightens a strap wrapped around the sides, front, and back of the user's head. Such conventional systems are ineffective for adjusting the size of the face shield and are cost ineffective for use in disposable applications.

BRIEF SUMMARY OF THE INVENTION

According to aspects of the invention, a protective face shield includes a substantially flat, at least partially transparent, waterproof sheet material of a shape extending over the face of a user, where the sheet material includes a portion configured to adjust the size of the sheet material. The adjustment portion may include predefined lines either drawn onto or impressed upon the sheet material and notches along an edge of the sheet material. The notches and predefined lines may be trimmed to allow a user to adjust a size and/or fit of the protective sheet material to the face of the user. The protective face shield may include an indicium corresponding to the size of the protective face shield, a manufacturer, a supplier, and/or specific information about a user.

Another aspect of the invention provides an adhesive component that secures the sheet material to the face of the user. The adhesive component may include double coated medical tape that secures the sheet material to the forehead of the user and/or beginning at the temples and down along the side of the user. Still other aspects of the invention have predefined lines parallel to an edge of the sheet material.

BRIEF DESCRIPTION OF THE DRAWINGS

A more complete understanding of the present invention and the advantages thereof may be acquired by referring to the following description in consideration of the accompanying drawings, in which like reference numbers indicate like features, and wherein:

FIGS. 4A-7B are illustrative views of face shield and adjustment systems and illustrative configurations on the face of a user in accordance with at least one aspect of the present invention;

DETAILED DESCRIPTION OF THE INVENTION

In the following description of the various embodiments, reference is made to the accompanying drawings, which form a part hereof, and in which is shown by way of illustration various embodiments in which the invention may be practiced. It is to be understood that other embodiments may be utilized and structural and functional modifications may be made without departing from the scope of the present invention.

Aspects of the present invention are directed to a protective face shield that includes an adjustment system. The protective face shield may be a substantially flat, tinted, and/or at least partially transparent sheet material. The sheet material also may be flexible, light weight, and/or waterproof with or without anti-fogging properties. The protective face shield permits a user to wash and take showers while protecting the areas of the face of the user being covered by the face shield. For example, aspects of the present invention may be used by optometrists and/or other doctors or hospitals to provide to patients after surgery. The face shield is designed to protect the user from getting areas of the face wet. The face shield may be used for protecting against exposure dust and/or dander as well. In accordance with at least one aspect of the present invention, the adjustment system on the protective face shield allows a user to configure the face shield to fit on the face of the user in a desired manner. As such, an adult and a child may use the same type of face shield and merely adjust, e.g., the face shield to a desired orientation on the particular user's face. A doctor may maintain a single protective face shield for all patients and configure the face shield to each patient as needed.

Figure 1:
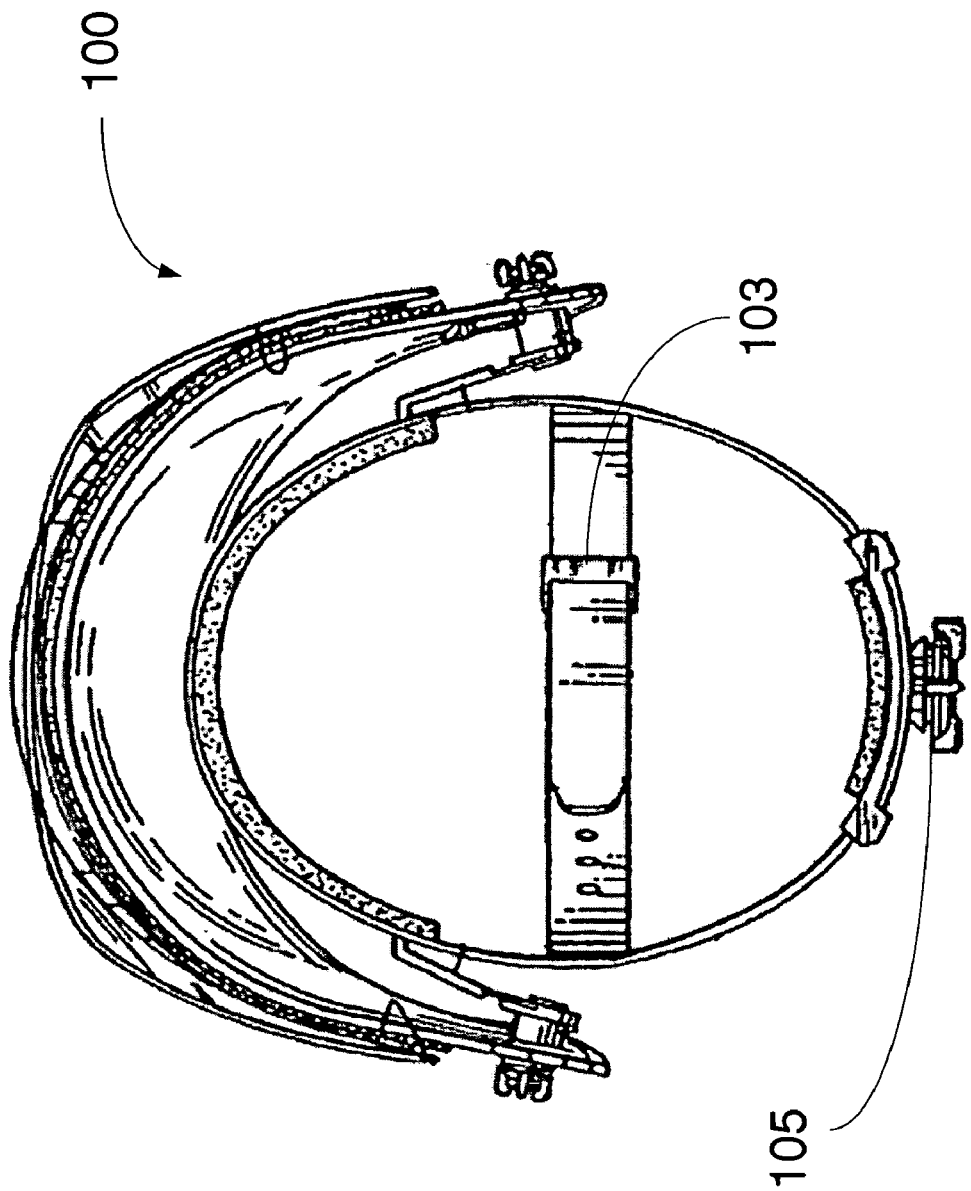
FIG. 1 is a plan view of a conventional face shield adjustment system.
Figure 2:
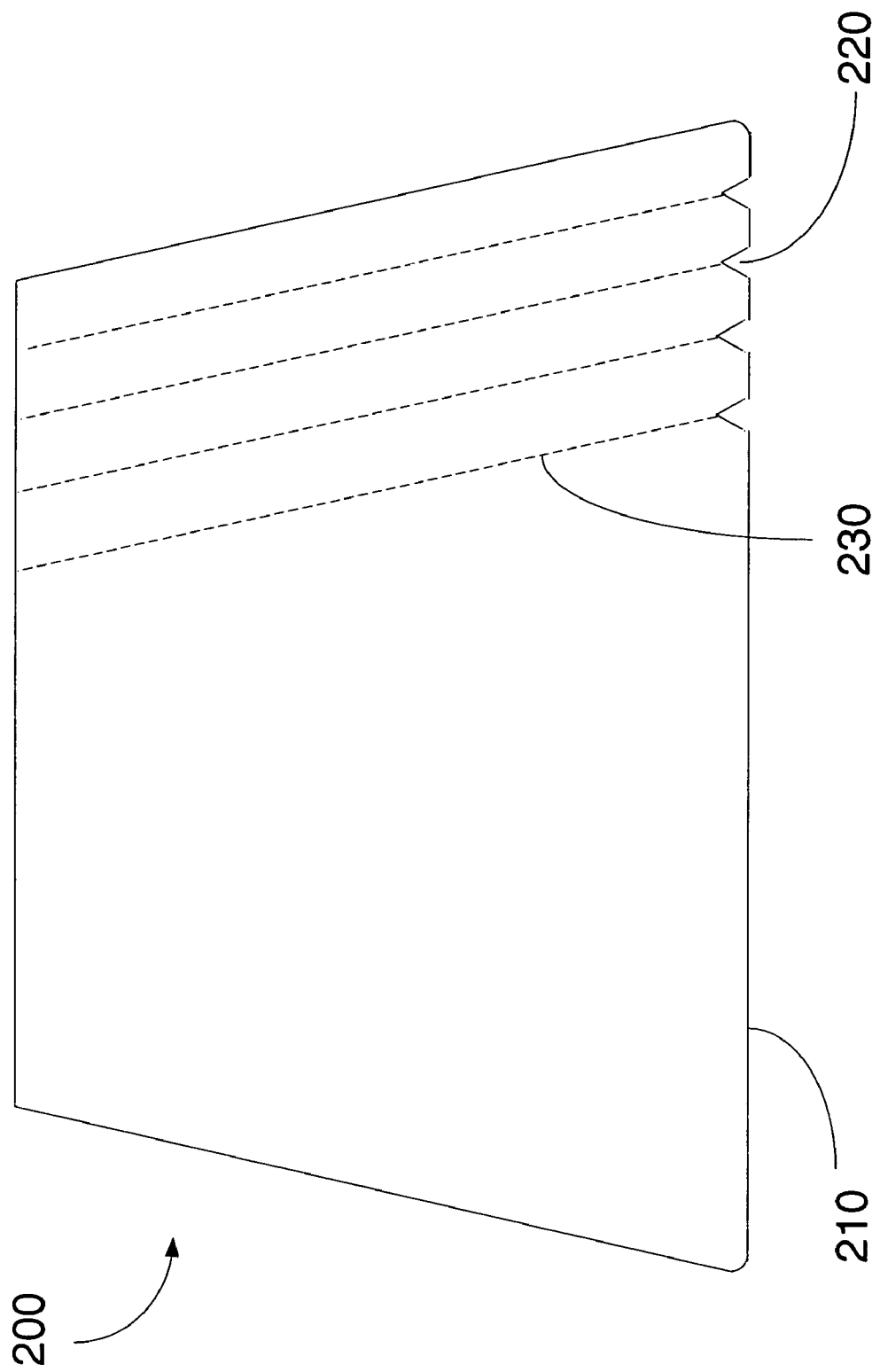
FIG. 2 is an illustrative view of a face shield and adjustment system in accordance with at least one aspect of the present invention.

FIG. 2 is an illustrative view of a face shield and adjustment by trimming system 200 in accordance with at least one aspect of the present invention. Protective face shield 200 is shown to include a substantially flat, at least partially transparent, and waterproof sheet material 210. Protective face shield 200 may be a disposable face shield for one time and/or short term use. Sheet material 210 may be sized to fit 5%-95% of face sizes of human beings. As shown, the adjustment system includes notches 220 in sheet material 210 and predefined lines 230. Predefined lines 230 guide a user, doctor, or adjuster, to adjust the size of sheet material 210 to a desired size. Predefined lines 230 are configured to be primarily out of the field of view of a user. Predefined lines 230 may be configured as perforated lines that allow a user to trim the sheet material 210 from the notches 220 and along the predefined lines 230 to adjust the size of the sheet material 210 to a desired size. In one embodiment, a user may tear along the perforated lines to adjust the size of the face shield 200. In one embodiment, a user may take a pair of scissors and trim the sheet material 210 along the predefined line 230. In another embodiment, predefined lines 230 may be configured as impressions or ink lines on the sheet material 210. Predefined lines 230 include perforated lines, ink lines, a series of holes, slits, or weakened areas, and/or any combination of these. As used herein, the term user includes an individual that wears the protective face shield and/or an individual that adjusts the protective face shield for another, such as a parent or a doctor.

Sheet material 210 may be made of a variety of different materials, including, but not limited to polypropylene, polystyrene, polycarbonate, rigid vinyl (RPVC) polyester, polyethylene, clear acetate plastic and/or polyvinyl chloride (PVC) material. Sheet material 210 may vary in thickness, length, width, and area. Sheet material 210 may include an anti-fogging treatment or composition to prevent fog or moisture on the surface of the sheet material. Additionally, sheet material 210 may be treated with a composition to maintain a sterile environment on the surface of the sheet material 210. Further, sheet material 210 may be tinted, thereby allowing a user to wear a colored face shield or protecting a user from the sun. Still further, sheet material 210 may be treated to protect a user against ultraviolet radiation. Notches 220 may be manufactured at the time of production of the sheet material 210 and/or at some other point during processing. Notches 220 may be an impressed area of sheet material 210 and/or an ink pattern configured to appear as a notch. Further, it should be understood by those skilled in the art that sheet material 210 need not include the notches 220 to allow for a guide in trimming the size of the face shield 200.

Figure 3:
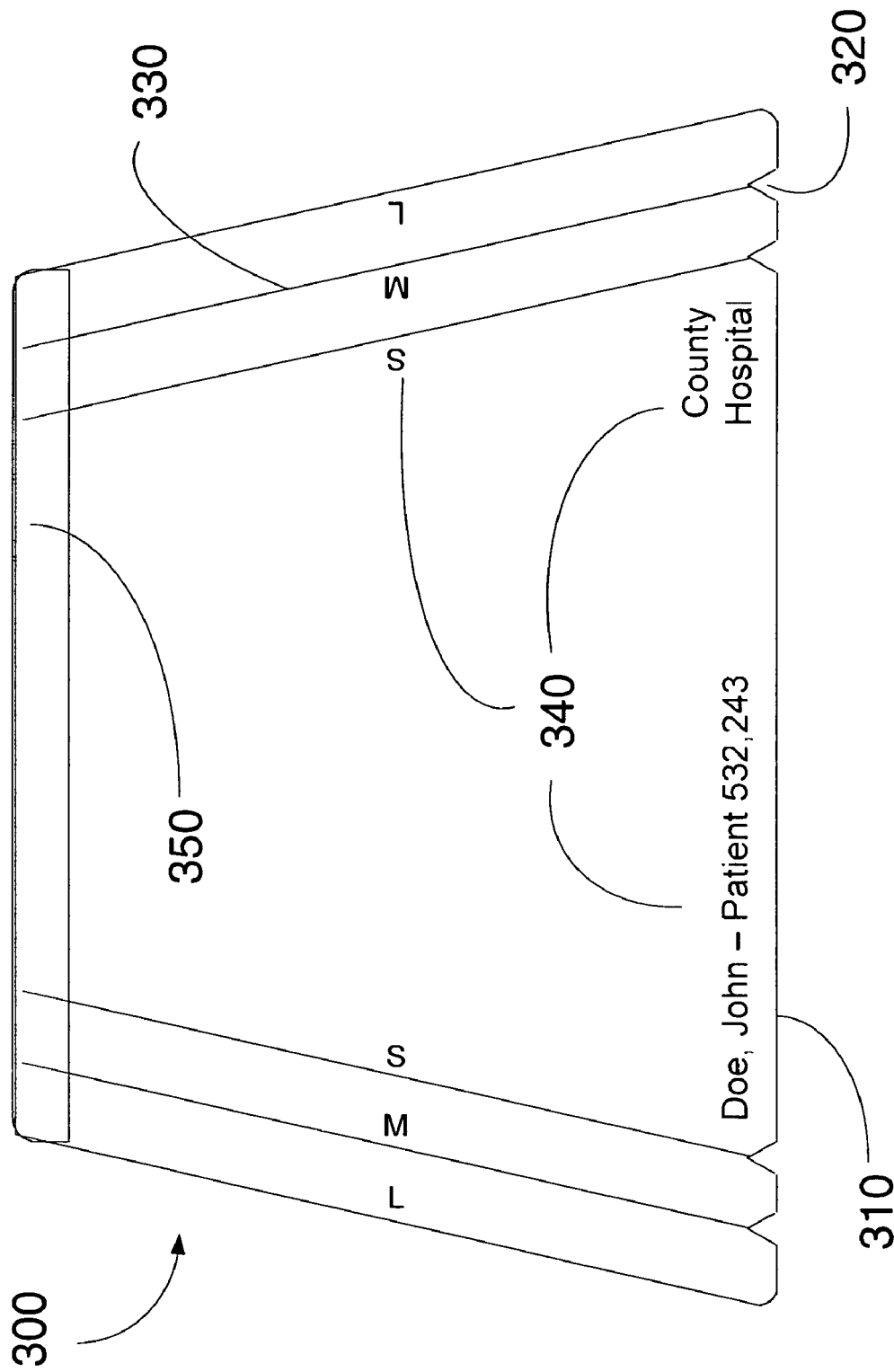
FIG. 3 is another illustrative view of a face shield and adjustment system in accordance with at least one aspect of the present invention.

FIG. 3 is another illustrative view of a face shield and adjustment system 300 in accordance with at least one aspect of the present invention. Protective face shield 300 is shown to include a substantially flat, at least partially transparent, and waterproof sheet material 310 similar to sheet material 210 in FIG. 2. As shown in FIG. 3, the adjustment system includes notches 320 in sheet material 310 and predefined lines 330. As described herein, predefined lines 330 guide a user, doctor, or adjuster, to adjust the size of sheet material 310 to a desired size. In the example shown in FIG. 3, predefined lines 330 are located along both sides of sheet material 310. A user can trim the sheet material 310 along the predefined lines 330 to a certain specified size (i.e., size indicium), e.g., "S" for small, "M" for medium, and "L" for large.

Protective face shield 300 also may include indicium 340. Indicium 340 may include manufactured indicium, such as the identification of a patient or name of a hospital providing the face shield. Indicium 340 also may include the size, "S", "M", or "L", of the face shield if a user trims along a corresponding predefined line 330. Sheet material 310 may also be configured to allow for the indicium to be written directly onto the face shield 300. For example, indicium 340 of "County Hospital" may be an impression or ink that was produced during manufacture, while indicium 340 of "Doe, John—U.S. Pat. No. 532,243" may be handwritten indicium specific to a user. As such, a hospital using proactive face shield 300 may have a mark specific to that hospital on the face shield 300. Other indicia 340 include trademarks, service marks and/or other information, such as a date to remove the face shield from the user.

Protective face shield 300 also is shown to include an adhesive component 350. Adhesive component 350 may include a piece of double coated tape, such as manufacturer's numbers 1577, 1509, 9874, 9889, and 1522 made by 3M Company of St. Paul, Minn. Other 3M Company and competitor tapes may be included as well. Adhesive component 350 may be a medical grade tape. Adhesive component 350 is configured to be applied to the top of the forehead of a user. Having trimmed, if needed, sheet material 310 to the desired size, a user can remove the protective backing on the adhesive component 350 and apply the protective face shield 300 to the top of the user's forehead. Although not shown in FIG. 3, adhesive material may additionally or alternatively be located along the sides of sheet material 310 thereby allowing a more secure and/or different fit to the face of a user.

Adhesive component 350 may include a tape liner thereby protecting the adhesive properties of one side of the double coated tape. The other side of the double coated tape may be secured against the top of sheet material 310 as shown in FIG. 3. Adhesive component 350 also may include an adhesive directly placed on sheet material 310. Such an adhesive may include a protective strip to prevent dust and debris from accumulating on the adhesive prior to application to the forehead of a user. The width of the adhesive component may vary. Adhesive component 350 may be applied to sheet material 310 during fabrication and/or by a user.

Protective face shield 300 may be fabricated in groups of face shields and bundled together for shipment, transport, delivery, and sales. Face shield 300 may be grouped together with adhesive components 350 grouped together in the same shipment. Adhesive component 350 may be added to sheet material 310 at the time of application to the face of a user and or anytime upon receipt at the point of delivery. Alternatively, protective face shield 300 may be grouped together for shipment with adhesive component 350 in place with a protective release strip to prevent the adhesive from contacting a surface prior to application to the forehead of a user.

Figure 4B:
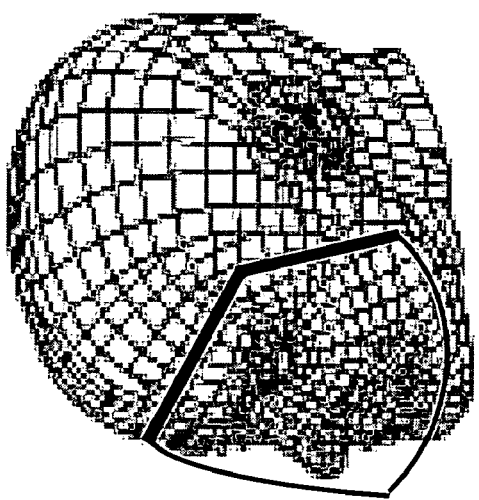
Figure 4A:
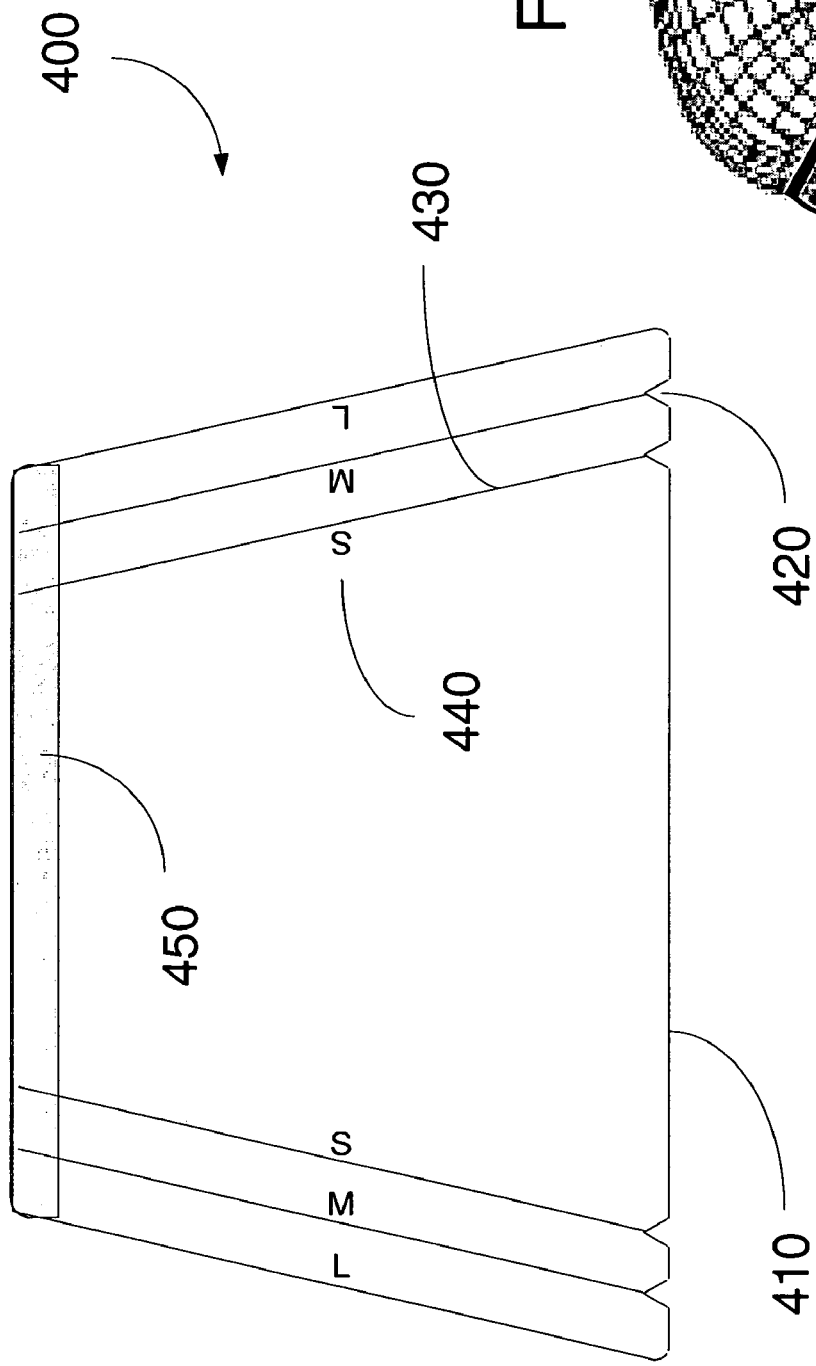
Figure 5B:
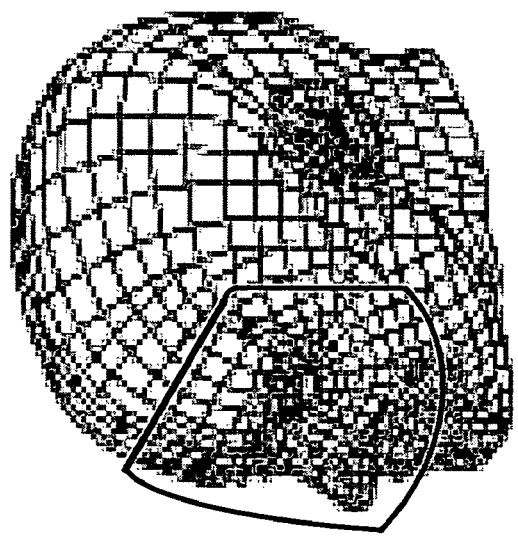
Figure 5A:
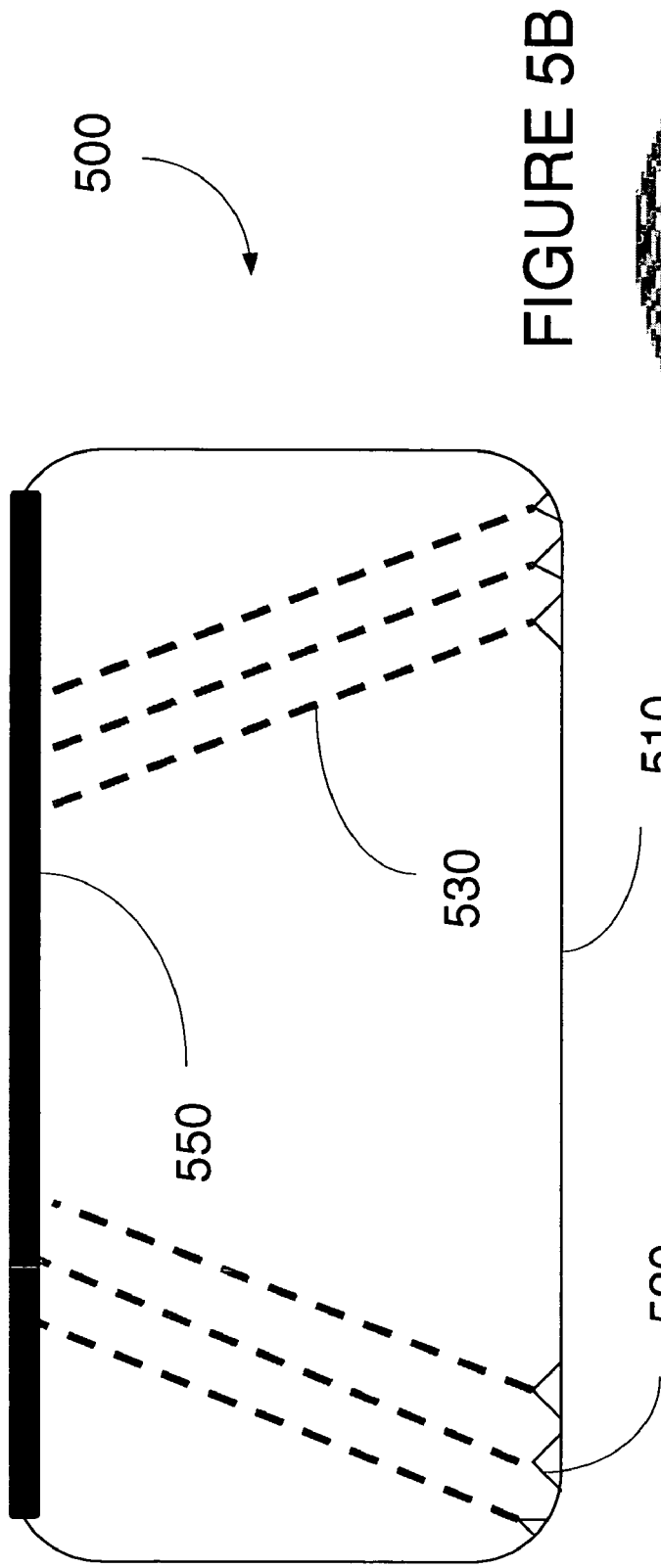

FIGS. 4A-7B are illustrative views of face shield and adjustment systems 400-700, respectively, and illustrative configurations on the face of a user in accordance with at least one aspect of the present invention. In FIG. 4A, a protective face shield 400 is shown in the general shape of a trapezoid. FIG. 4B shows an illustrative perspective view of the face shield 400 during use as seen from the left side of a user. In FIG. 5A, a protective face shield 500 is shown in the general shape of a rectangle. FIG. 5B shows an illustrative perspective view of the face shield 500 during use as seen from the left side of a user. In FIG. 6A, a protective face shield 600 is shown in the general shape of an oval. FIG. 6B shows an illustrative perspective view of the face shield 600 during use as seen from the left side of a user. As shown, portion 660 may be trimmed for a better fit against the forehead of a user. In FIG. 7A, a protective face shield 700 is shown in the general shape of a circle. FIG. 7B shows an illustrative perspective view of the face shield 700 during use as seen from the left side of a user. As shown, portion 760 may be trimmed for a better fit against the forehead of a user.

Figure 8A:
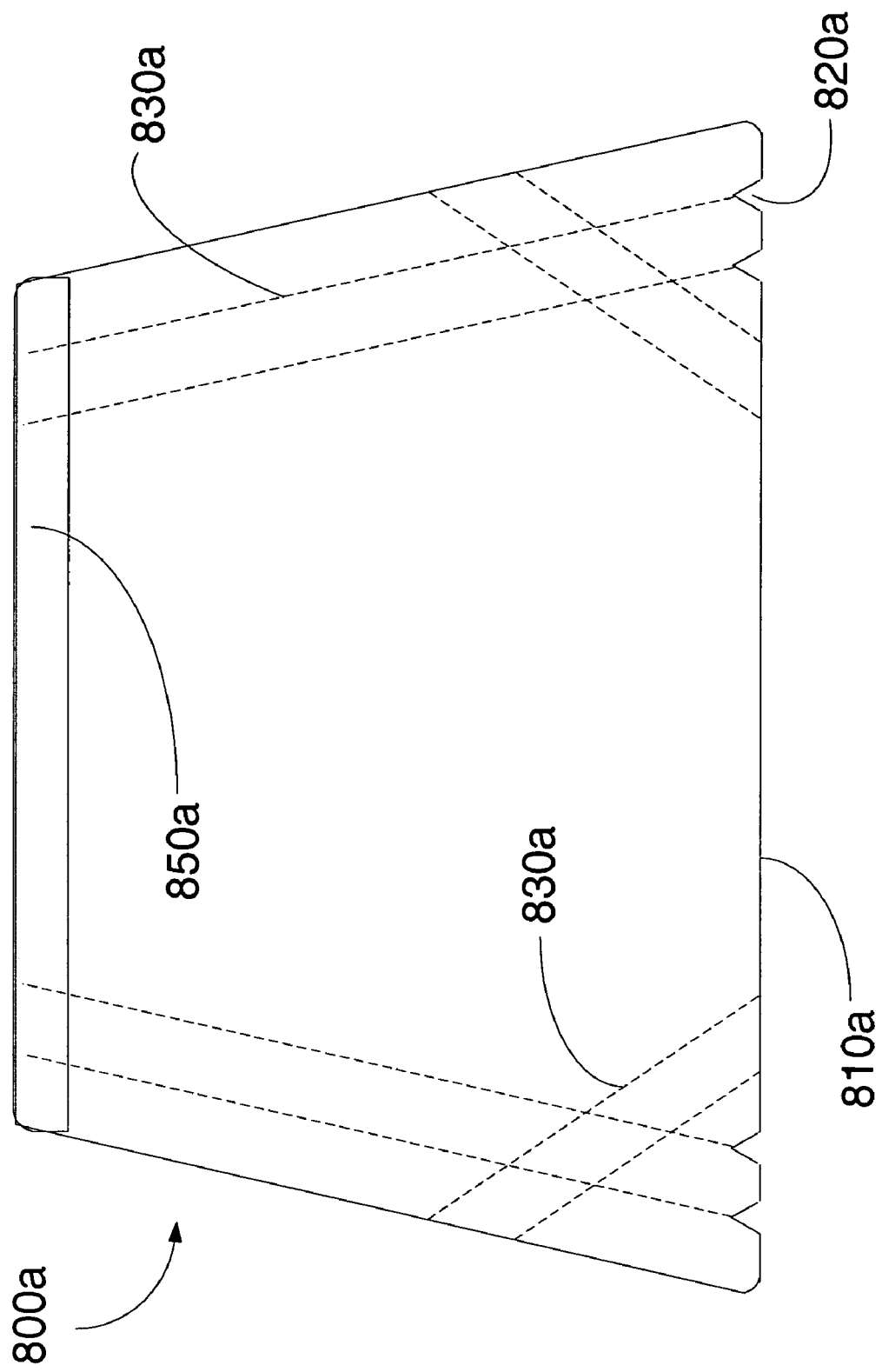
FIGS. 8A-8B are further illustrative views of face shield and adjustment systems in accordance with at least one aspect of the present invention.
Figure 8B:
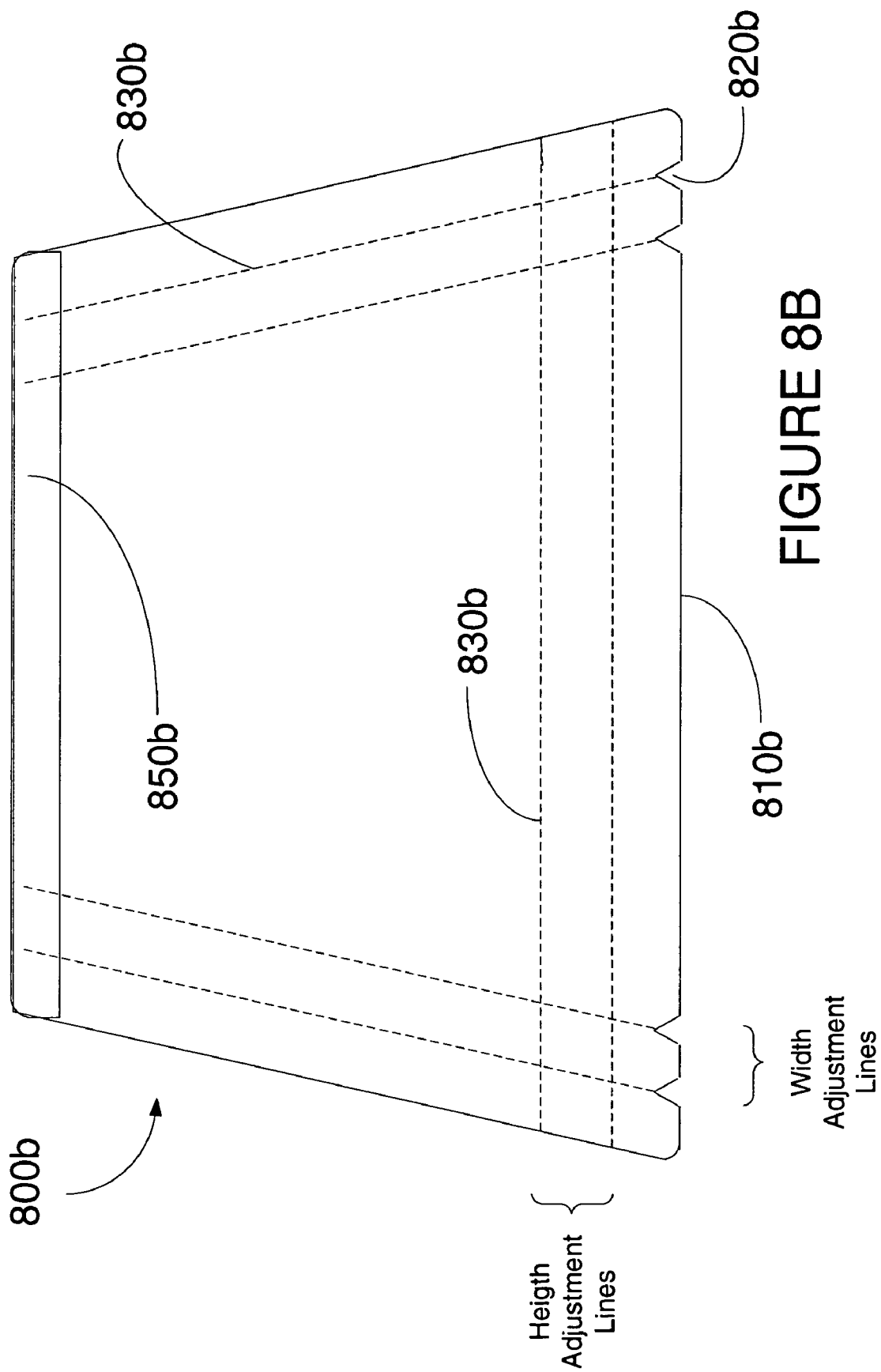

FIGS. 8A-8B are further illustrative views of face shield and adjustment systems 800a and 800b in accordance with at least one aspect of the present invention. Protective face shield 800a is shown to include sheet material 810a, notches 820a, predefined lines 830a and adhesive component 850a as similar shown in FIG. 3. In FIG. 8A, redefined lines 830a are shown in a different configuration, allowing a user to trim sheet material 810*a* to create a different shape that may be desired by the user. FIG. 8B illustrates another example configuration of the predefined lines 830*b*. As shown in FIG. 8B, predefined lines 830*b* also are oriented along the bottom of sheet material 810*b* and parallel to the bottom edge of the sheet material 810*b* allowing a user to trim to a smaller length as desired by the user. As shown, some of the predefined lines 830*b* may be configured to allow for adjustment of the height of the face shield 800*b* while others may be configured to allow for adjustment of the width of the face shield 810*b*.

While illustrative systems and methods as described herein embodying various aspects of the present invention are shown, it will be understood by those skilled in the art, that the invention is not limited to these embodiments. Modifications may be made by those skilled in the art, particularly in light of the foregoing teachings. For example, each of the elements of the aforementioned embodiments may be utilized alone or in combination or subcombination with elements of the other embodiments. It will also be appreciated and understood that modifications may be made without departing from the true spirit and scope of the present invention. The description is thus to be regarded as illustrative instead of restrictive on the present invention. Many components, such as the adhesive component 350, predefined lines 330, and notches 320 may be varied. The present invention is not limited to any one example included herein and various other configurations and orientations may be utilized while still maintaining the scope of the true spirit and scope of the present invention.

We claim:

1. A disposable protective face shield system comprising:
   a substantially flat, at least partially transparent, waterproof sheet material of a generally trapezoidal shape configured to extend over a portion of the face of a user;
   a piece of double coated medical tape configured to secure the protective face shield to at least the forehead of the user, the piece double coated medical tape including a peelable release strip;
   wherein the sheet material includes:
   a set of predefined lines and notches configured to assist the modification of the size of the sheet material, and
   a set of indicium corresponding to the predefined lines and notches, wherein the indicium describes a correlated size of the protective face shield.

2. The protective face shield system of claim 1, wherein the piece of double coated medical tape has a first side directly connected to the sheet material.

3. The protective face shield system of claim 1, wherein the set of predefined lines includes at least one perforated line.

4. The protective face shield system of claim 1, wherein the set of predefined lines includes at least one ink line.

5. The protective face shield system of claim 1, wherein at least one predefined line of the set of predefined lines is located parallel to at least one edge of the sheet material.

6. The protective face shield system of claim 1, wherein at least one predefined line of the set of predefined lines is located parallel to at least one edge of the sheet material and at least one other predefined line is located parallel to at least one other edge of the sheet material.

7. The protective face shield system of claim 1, wherein the set of predefined lines includes two predefined lines along one side of the sheet material and two predefined lines along an opposite side of the sheet material.

8. The protective face shield system of claim 1, wherein the sheet material is a polyester material.

9. The protective face shield system of claim 1, wherein the sheet material further includes an indicium corresponding to the user.

10. The protective face shield system of claim 1, wherein the sheet material further includes an anti-fogging treatment.

11. The protective face shield system of claim 1, wherein the sheet material is tinted.

12. The protective face shield system of claim 1, wherein the sheet material further includes a composition to maintain a sterile environment.

\* \* \* \* \*